US00PP35957P2

(12) United States Plant Patent
van der Voort

(10) Patent No.: US PP35,957 P2
(45) Date of Patent: Jul. 2, 2024

(54) ***AGASTACHE* PLANT NAMED 'AGAPK'**

(50) Latin Name: ***Agastache* hybrid**
Varietal Denomination: Agapk

(71) Applicant: Van Hemert & Co. BV, Hazerswoude (NL)

(72) Inventor: Rob van der Voort, Hazerswoude (NL)

(73) Assignee: VAN HEMERT & CO. BV, Hazerswoude (NL)

( * ) Notice: Subject to any disclaimer, the term of this patent is extended or adjusted under 35 U.S.C. 154(b) by 0 days.

(21) Appl. No.: 18/510,510

(22) Filed: Nov. 15, 2023

(30) Foreign Application Priority Data

May 3, 2023 (QZ) ..... PBR 2023/0969

(51) Int. Cl.
*A01H 5/02* (2018.01)
*A01H 6/50* (2018.01)

(52) U.S. Cl.
USPC ..... Plt./399

(58) Field of Classification Search
USPC ..... Plt./263.1, 399
See application file for complete search history.

*Primary Examiner* — Karen M Redden
(74) *Attorney, Agent, or Firm* — Penny J. Aguirre

(57) ABSTRACT

A new cultivar of *Agastache* plant named 'Agapk' that is characterized by its good performance in humid climates, its abundance of flowers that are pink in color and become dark purple-pink in color in autumn, its foliage that is dark green in color, its compact and well branched plant habit, its good winter hardiness, and its ability to be readily and quickly produced by cuttings.

3 Drawing Sheets

Botanical classification: *Agastache* hybrid.
Variety denomination 'Agapk'.

CROSS REFERENCE TO A RELATED APPLICATION

This application claims priority to European Community Plant Variety Office (CPVO) Plant Breeder's Rights Application No. 2023/0969 filed on May 3, 2023, under 35 U.S.C. 119(f), the entire contents of which is incorporated by reference herein.

BACKGROUND OF THE INVENTION

The present invention relates to a new and distinct cultivar of *Agastache* hybrid and will be referred to hereafter by its cultivar name, 'Agapk'. 'Agapk' is an herbaceous perennial grown for landscape use.

'Agapk' arose as part of an ongoing breeding program conducted by the Inventor in Hazerswoude, The Netherlands. The goal of the breeding program is to develop new cultivars of *Agastache* with well-branched and compact plant habits, healthy foliage, floriferous blooming habits, resistance against fungal diseases, and long flower spikes with pink flowers that remain attractive in autumn.

'Agapk' derived from a controlled cross between unnamed and unpatented proprietary plants of *Agastache* from the Inventor's breeding program in August of 2016. The new cultivar was selected from amongst the resulting seedlings as a single unique plant in August of 2017.

Asexual propagation of the new cultivar was first accomplished by the Inventor by stem cuttings in 2018 in Hazerswoude, The Netherlands. Asexual propagation of the new cultivar by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Agapk' as a unique cultivar of *Agastache*.

1. 'Agapk' exhibits good performance in humid climates (a problem with many *Agastache* cultivars).
2. 'Agapk' exhibits an abundance of flowers that are pink in color and become dark purple-pink in color in autumn.
3. 'Agapk' exhibits foliage that is dark green in color.
4. 'Agapk' exhibits a compact and well branched plant habit.
5. 'Agapk' exhibits good winter hardiness.
6. 'Agapk' exhibits the ability to be readily and quickly produced by cuttings.

Both the female and male parents of 'Agapk' are similar to 'Agapk' in having pinkish flowers and the female parent is also similar in plant habit. Both parent plants of 'Agapk' differ from 'Agapk' in having flowers that are more purple in color and the male parent of 'Agapk' also differs from 'Agapk' in having a larger plant size. 'Agapk' can be compared to the *Agastache* cultivars 'Agapd' (U.S. Plant Pat. No. 30,614) and 'Blue Fortune' (not patented). 'Agapd' and 'Blue Fortune' are both similar to 'Agapk' in having an abundance of flowers. 'Agapd' differs from 'Agapk' in having less branching and flower panicles that are smaller in size with pink flowers that become dark purplish pink in autumn. 'Blue Fortune' differs from 'Agapk' in having less branching and flower panicles that are smaller in size with pale blue flowers.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Concept Plants, Plantago, Green Service Plants, The Plant Group, YouTube (Peter Plantipp), Kientzler, PennState College of Agricultural Sciences, Barnes Nurseries, Nova, Plantentuin, Esveld, Kwekerij De Hessenhof, Florapont, Stauden Stade, De Bloeimeesters, Globe Planter, Opvallende, Instagram (Peter van Rijssen, Greenhouse Grower, Greenhouse Management, eplant Source, and Griffin Greenhouse Supplies (Innova Plant).

BRIEF DESCRIPTION OF THE DRAWINGS

The accompanying color photographs illustrate the overall appearance and distinct characteristics of 1-year-old plants of the new *Agastache* as grown in trial gardens. The photograph in FIG. 1 was grown in Nieuwveen, The Netherlands and the photographs in FIG. 2 and FIG. 3 were grown in Heerhugowaard, The Netherlands.

The photograph in FIG. 1 provides a side view of 'Agapk' in bloom.

Figure 1:
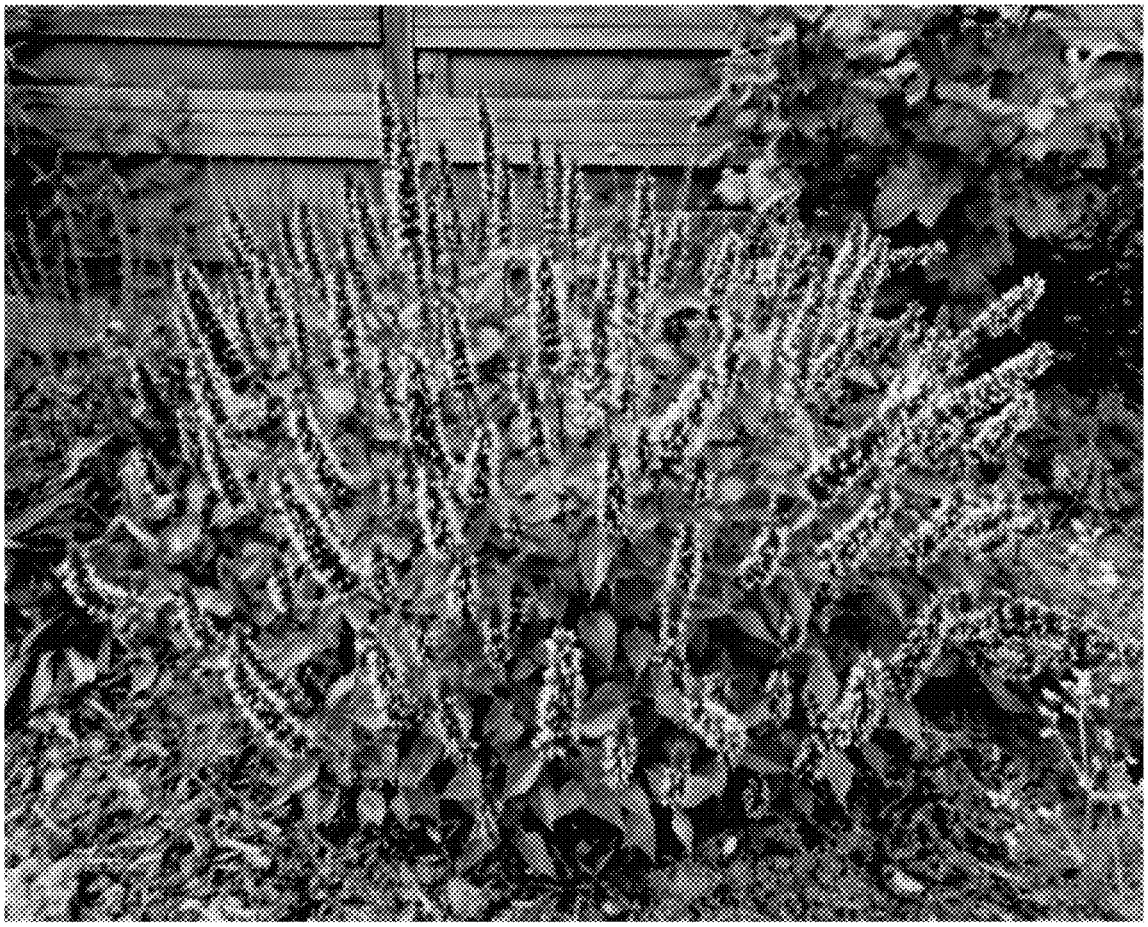
Figure 2:
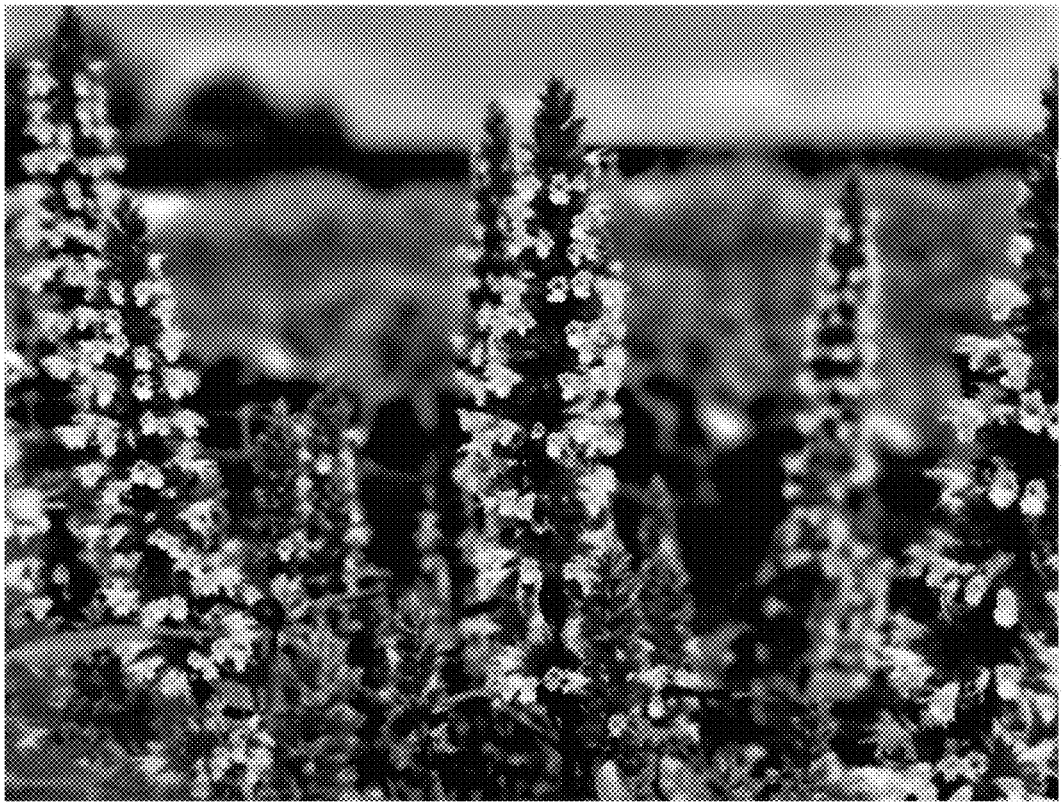

The photograph in FIG. 2 provides a close-up view of an inflorescence of 'Agapk'.

Figure 3:
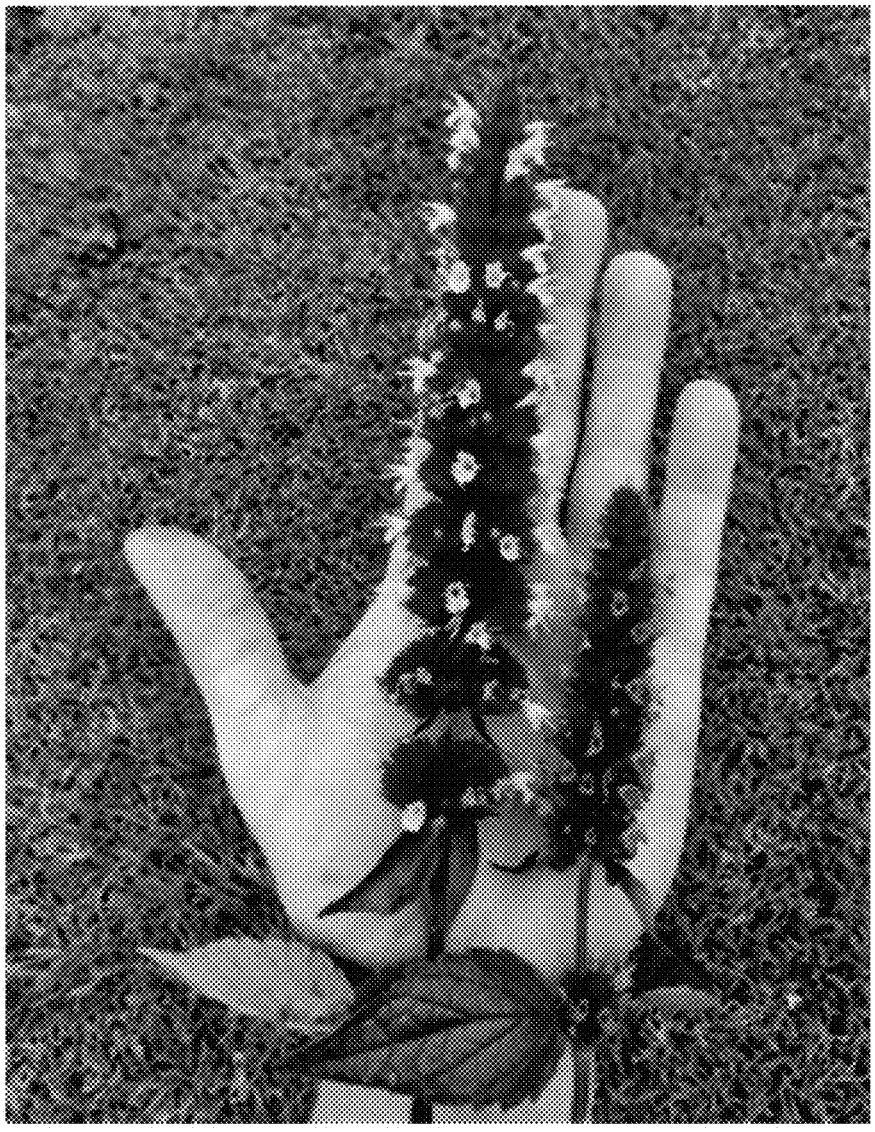

The photograph in FIG. 3 provides a comparison view of an inflorescence of 'Agapk' (left) with an inflorescence of 'Agapd' (right).

The colors in the photographs may differ slightly from the color values cited in the detailed botanical description, which accurately describe the colors of the new *Agastache*.

DETAILED BOTANICAL DESCRIPTION

The following is a detailed description of the new cultivar of plants 1 year in age as grown outdoors in 19-cm containers in Lier, Belgium. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—July through September in The Netherlands.

*Plant type*.—Herbaceous perennial.

*Plant habit*.—Upright, broadly spreading.

*Plant size*.—Average of 45 cm in height and 36 cm in width as a one-year-old plant in a container, reaches 70 cm in height and 50 cm in spread in the landscape.

*Cold hardiness*.—At least in U.S.D.A. Zones 6b to 11.

*Diseases and pests*.—No susceptibility or resistance to diseases or pests has been observed.

*Root description*.—Fibrous and fine.

*Root development*.—About 4 to 5 weeks to initiate roots and 6 to 8 weeks to fully root as a young plant.

*Propagation*.—Stem cuttings.

*Growth rate*.—Moderate to high.

Stem description:

*Shape*.—Quadrangular.

*Stem color*.—Main; 144A, flushed with N199A, lateral; 144A to 144B, flushed with 183A.

*Stem size*.—Up to 37 cm in length, 6 mm in diameter.

*Stem surface*.—Slightly glossy and slightly pubescent.

*Stem aspect*.—Held at varying angles between 50° to 80°.

*Internode length*.—Average of 2.5 cm.

*Branching*.—Average of 6 main branches and 3 lateral branches per main stem.

*Stem strength*.—Moderately strong.

Foliage description:

*Leaf shape*.—Ovate.

*Leaf division*.—Simple.

*Leaf base*.—Truncate.

*Leaf apex*.—Acuminate.

*Leaf venation*.—Pinnate, young upper surface color; 143A, young lower surface color; 143D, mature upper surface color; 138A, mature lower surface color; 138B and 138C, hint of 183A.

*Leaf margins*.—Serrate.

*Leaf arrangement*.—Opposite.

*Leaf attachment*.—Petiolate.

*Leaf surface*.—Both surfaces matte and densely pubescent.

*Leaf size*.—Average of 6.3 cm in length and 4.4 cm in diameter.

*Leaf color*.—Young upper surface; 143A, young lower surface; 143C, mature upper surface; 138A, mature lower surface; 138B.

*Fragrance*.—Strong minty fragrance.

*Petioles*.—An average of 3 cm in length and 2 mm in diameter, color; both surfaces 138A, moderately strong, both surfaces are smooth and densely pubescent.

Inflorescence description:

*Inflorescence type*.—Terminal raceme.

*Lastingness of inflorescence*.—Individual flowers average of 10 days, self cleaning.

*Inflorescence size*.—An average of 8.5 cm in height and 4.3 cm in diameter.

*Flower type*.—Labiate.

*Flower aspect*.—Outward, freely flowering.

*Flower number*.—Average of up to 200 flowers and buds per inflorescence.

*Flower fragrance*.—None.

*Flower buds*.—Obovate in shape, 5 mm in length, 3 mm in diameter, smooth and glabrous surface, immature petals and free calyx tips color; 70A and 70B, tube 145B to 145C, immature calyx N66D.

*Flower size*.—Average of 1.7 cm in height, 6 mm in width.

*Peduncle*.—An average of 8 cm in length and 3 mm in diameter, 144B in color, held straight on top of lateral branch, moderately strong in strength, surface is densely pubescent.

*Pedicels*.—Average of 2 mm in length, 1 mm in diameter, 144C in color.

*Calyx*.—Rotate and tubular in shape, average of 7 mm in length and 3 mm in diameter.

*Sepals*.—5, rotate, 1 whorl, base is fused, obovate in shape, entire margin, acute apex, 7 mm in length, 1 mm in width, entire margins, upper and lower surface smooth, glabrous, color; when opening and fully open upper surface 75B, when opening and fully open lower surface 75B, tube 75C and 75D.

*Petals.*—5, 1 whorl, fused into tube, oblanceolate in shape, obtuse apex, lower petal has 2 lobes, entire margins, surfaces are glabrous, color; when opening and fully open upper surface 75B, when opening and fully open lower surface 75B, tube 75C and 75D.

Reproductive organs:

*Gynoecium.*—Pistil; 1, 1.6 cm in length, 0.5 mm in width, style; 1.5 cm in length, 75D, base NN155D in color, stigma; cleft (2 parted), 0.5 mm in diameter and 75D in color, ovary; N144A to 144B in color.

*Androecium.*—Stamens; 4, filaments; 1.4 cm in length, 0.5 mm in width, color; 75D, base NN155D, anthers; dorsifixed, 0.5 mm in length and width, 77A in color, pollen; low to moderate, color is not clearly visible.

*Fruit and seed.*—None have been observed.

It is claimed:

1. A new and distinct cultivar of *Agastache* plant named 'Agapk' as herein illustrated and described.

* * * * *